(12) United States Patent
Silver

(10) Patent No.: US 6,673,037 B1
(45) Date of Patent: Jan. 6, 2004

(54) BREASTPUMP SHIELDS HAVING MODIFIED SHAPE

(75) Inventor: Brian H. Silver, Caay, IL (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 09/722,840

(22) Filed: Nov. 27, 2000

(51) Int. Cl.$^7$ .............................................. A61M 1/06
(52) U.S. Cl. ..................................................... 604/74
(58) Field of Search ..................... D24/109; 604/73–76

(56) References Cited

U.S. PATENT DOCUMENTS

| | | | | |
|---|---|---|---|---|
| 3,822,703 A | | 7/1974 | Davisson | 128/281 |
| 4,680,028 A | | 7/1987 | Stuart | 604/74 |
| 4,772,262 A | * | 9/1988 | Grant et al. | 604/74 |
| 4,794,915 A | * | 1/1989 | Larsson | 604/75 |
| 4,813,932 A | | 3/1989 | Hobbs | 604/74 |
| 4,857,051 A | | 8/1989 | Larsson | 604/74 |
| 4,929,229 A | | 5/1990 | Larsson | 604/74 |
| 4,950,236 A | | 8/1990 | Wilson | 604/74 |
| 5,049,126 A | | 9/1991 | Larsson | 604/74 |
| 5,100,406 A | * | 3/1992 | Panchula | 604/74 |
| 5,258,041 A | | 11/1993 | Guire et al. | 623/66 |
| 5,749,850 A | | 5/1998 | Williams et al. | 604/74 |
| 5,776,177 A | | 7/1998 | MacWhinnie et al. | 607/108 |
| 5,885,246 A | * | 3/1999 | Ford | 604/74 |
| 5,897,580 A | | 4/1999 | Silver | 607/108 |
| 5,902,293 A | | 5/1999 | Liu | 604/313 |
| 5,941,847 A | | 8/1999 | Huber et al. | 604/74 |
| D418,598 S | * | 1/2000 | Jauch | D24/109 |
| D446,852 S | * | 8/2001 | Johansen et al. | D24/109 |
| D446,853 S | * | 8/2001 | Johansen et al. | D24/109 |
| 6,273,868 B1 | * | 8/2001 | Nordvik | 604/74 |
| D456,897 S | * | 5/2002 | Atkin et al. | D24/100 |
| 6,383,164 B1 | * | 5/2002 | Johansen et al. | 604/74 |

* cited by examiner

Primary Examiner—Sharon Kennedy
(74) Attorney, Agent, or Firm—Baniak Pine & Gannon

(57) ABSTRACT

An improved breastshield for breastpumps has a tubular extension with a non-circular internal contour such as an oval, polygonal or fluted shape, among others. In another aspect of the invention, the non-circular contour is provided in the main breast-receiving part of the breastshield. Surface features, such as protuberances, are further provided for the breastshield which yield a non-smooth tactile feel to the breastshield.

5 Claims, 3 Drawing Sheets

BREASTPUMP SHIELDS HAVING MODIFIED SHAPE

FIELD OF THE INVENTION

The invention relates to breastshields for breastpumps.

BACKGROUND OF THE INVENTION

Breastpumps are well known, and generally are comprised of breastshields (also referred to as hoods) that fit over the breast, a vacuum pump connected to the breastshield for generating an intermittent vacuum within the breastshield, and a receptacle for the milk that is pumped from the breast. Manually driven vacuum pumps are commonplace, as well as those that are driven by a motor (house current, battery, pneumatic, etc.).

The vacuum pumps of these devices intermittently generate a vacuum (or negative pressure) within the breastshield, with the breastshield covering the nipple and typically a substantial amount of the breast itself. The intermittent suction action of the pump serves to pull on and compress the breast, and thereby extract milk in an action similar to suckling. The milk so extracted ordinarily flows from the breastshield into a collection container, e.g., a bottle, for storage and later use. A breastpump of the foregoing description is shown in U.S. Pat. Nos. 4,857,051, and 4,929,229, and reference thereto may be made for further detail on breastpumps in general.

Breastshields typically have a funnel-shape, comprising a conical portion with a tubular extension, sometimes referred to as the nipple tunnel. The nipple and surrounding breast are received in the conical portion, with the nipple often extending into the tubular extension. Under vacuum, the breast is pulled further into the breastshield, ordinarily with the nipple then being pulled into the tubular extension, with the surrounding breast thereby also compressed about the nipple.

A nursing mother's nipples may thus be forced against the wall of the nipple tunnel under vacuum. This may cause friction against the wall as the nipple moves deeper into the nipple tunnel. There can also be friction between the breast and the conical portion, as well as the nipple tunnel.

Breastshields have traditionally been made using a regularly shaped conical portion and nipple tunnel. That is, the conical portion is a geometric cone, with a smooth interior wall having a circular axial cross-section. The nipple tunnel is likewise smooth-walled, with a circular cross-section. Breastshields have also traditionally utilized a conical portion having a single slope angle (i.e., a single angle of revolution for the frustoconical part). An abrupt, and typically sharp-angled, transition is used between the conical portion and the tubular extension.

SUMMARY OF THE INVENTION

It is a principal objective of the invention to provide an improved breastshield for breastpumps. To that end, one aspect of the invention comprises a breast-receiving part, typically having a cone-shaped portion with a truncated apex forming an upstream opening in the cone, an exterior and an interior. A tubular extension, or tunnel, extends from the apex opening of the cone, ordinarily along a common longitudinal axis with the cone. The entrance of the tubular extension has an inlet proximal thereto, which communicates with the apex opening of the cone. As will be noted hereafter, other non-conical shapes for the breast-receiving part can be utilized.

In one form of the invention, the interior of the tubular extension is provided with an irregular shape, with the irregular shape preferably (but not necessarily) starting adjacent the opening of the tubular part and extending some or all of the length of the tubular extension. The interior cross-sectional shape in certain embodiments may be triangular, squarish, oval, pentagonal, and the like, all of which are non-traditional shapes (e.g., non-circular) for the nipple tunnel. In addition, or alternatively, the interior sidewall of the tubular extension may be provided with a non-circular (in radial cross-section) surface contour of, for instance, smoothly undulating peaks and valleys taking on a fluted shape. Bumps, ridges and other protuberances, most preferably fixed in shape, whether in a regular or irregular pattern, may be provided in another variant. It will be additionally noted that the foregoing non-traditional shapes and surface contours may advantageously extend into the conical (i.e., breast-receiving) part of the breastshield.

In another aspect of the invention, the inlet to the interior of the tubular extension is provided with a less abrupt transition surface from the conical portion. This transition surface between the conical portion and the tubular extension takes the form, in one embodiment, of a chamfered transition surface. In this latter embodiment, the main area of the conical portion has a first slope, with an intermediate area between the main area and the tubular extension having a second slope, with the second slope selected to provide an intermediate gradient between conical portion and nipple tunnel entrance.

It is anticipated that the foregoing non-circular contours for the tubular extension interior will have beneficial effects upon the milk expression process. In many respects, these shapes are reminiscent of various mouth and tongue positions of a baby during suckling. The aspect of the invention wherein a chamfered and therefore less abrupt transition is provided between the conical portion and tubular extension is likewise expected to have a salutary effect, at a minimum, reducing the pressure on the breast/nipple at this transition and providing a more comfortable device.

These and other aspects and advantages of the present invention will be further appreciated and understood upon consideration of the detailed description of various embodiments of the invention taken in conjunction with the drawings, in which:

DETAILED DESCRIPTION OF EMBODIMENTS OF THE INVENTION

Figure 1:
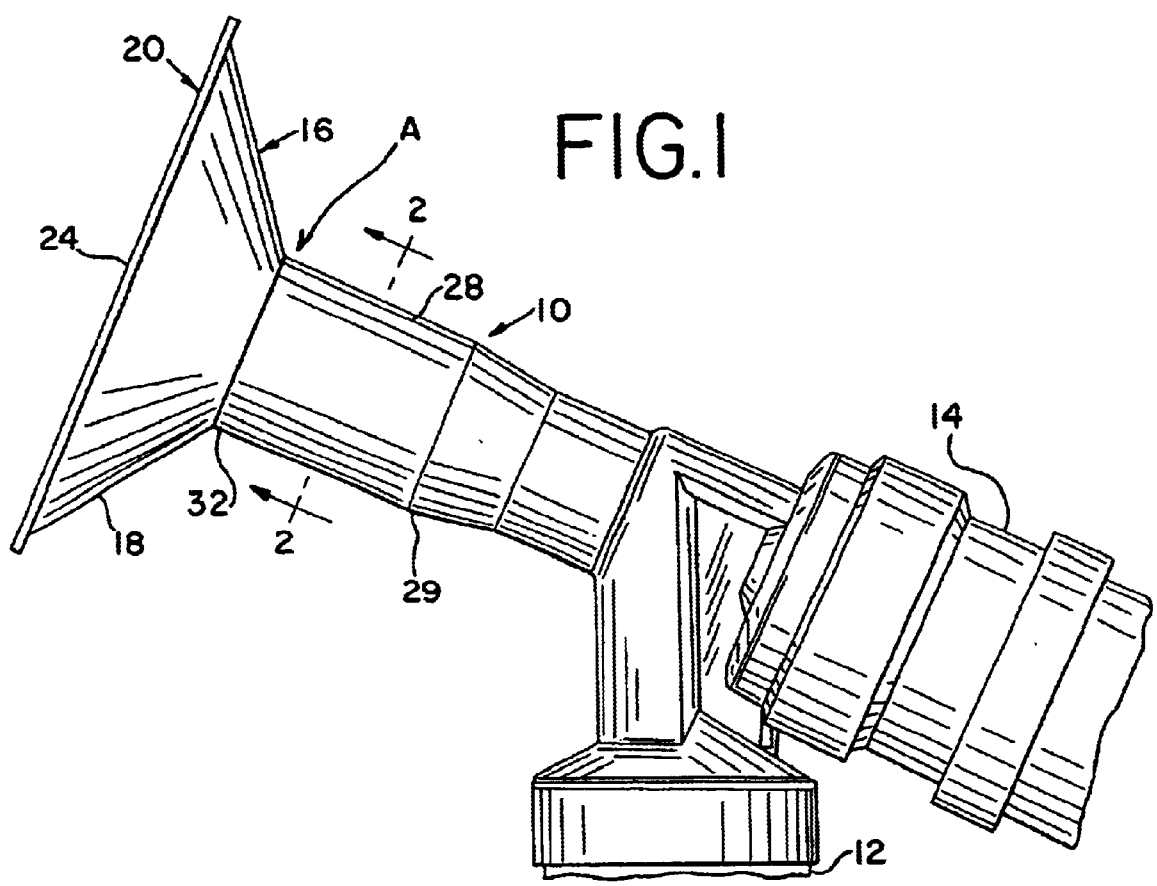
FIG. 1 is a horizontal side view of the exterior of a breastshield.

FIG. 1 shows a breastshield assembly and is designated generally by the number 10. Shown partially are the milk collection container 12 and a manual piston pump 14. The breastshield has a breast-receiving cone or conical portion 16 having an exterior 18 and an interior 20. The cone 16 has a base 24 and a truncated apex at A. Connected to the truncated apex A is a tubular extension or nipple tunnel 28, the proximal part thereof comprising an entrance or inlet 32 to the tubular extension 28. The cone 16 and tubular tunnel 28 have a common longitudinal axis in this embodiment.

The interior of the entrance 32 is configured so that it has an irregular shape, that is, it is non-circular in general shape and/or with a non-circular interior sidewall contour 34. This irregular shape may come in a variety of types, such as those illustrated in FIGS. 2a–2h. The irregular shape preferably starts somewhere adjacent opening 32 to the distal end 29 of the tubular tunnel 28. It need not extend that far, however, but it is considered desirable for the shape to extend at least along the length where contact with the nipple/breast is likely to occur. These irregular shapes would be typically formed directly within the nipple tunnel 28 in the breast shield molding process.

Figure 2A:
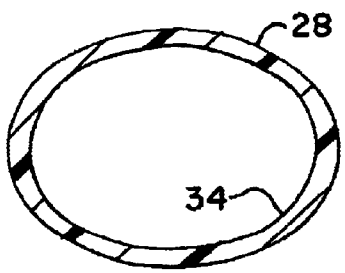
FIGS. 2a–2h are enlarged cross-sectional views taken across the line 2—2 of FIG. 1, and illustrate a number of different non-circular shaped configurations for a tubular extension made in accordance with the invention.
Figure 2B:
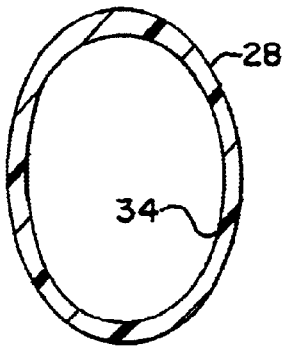

FIG. 2a shows an oval shape for the tubular extension 28 interior and exterior. This oval shape has its long axis in a horizontal plane relative to its orientation in use. FIG. 2b illustrates a like oval shape, this time with its long axis oriented in a vertical plane.

Figure 2C:
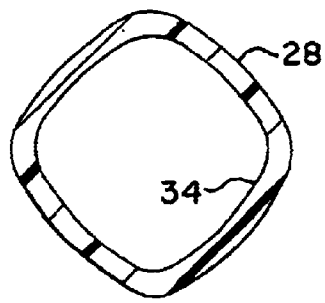
Figure 2D:
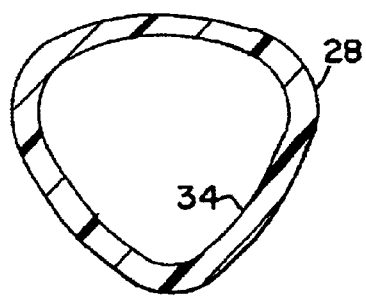
Figure 2E:
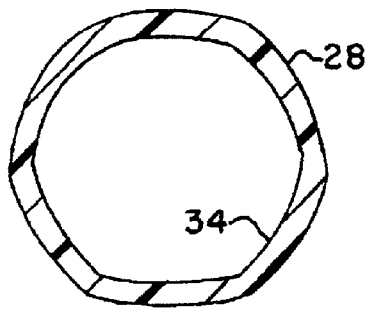

FIG. 2c is an embodiment having a generally squarish cross-sectional shape to the tubular extension 28 as well as the interior sidewall 34. FIG. 2d has a generally triangular tubular extension 28. FIG. 2e has a six-sided polygonal shape to the tubular extension 28, including its interior sidewall 34.

Figure 2F:
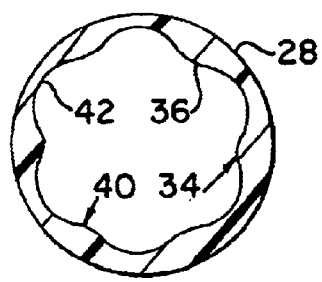
Figure 2G:
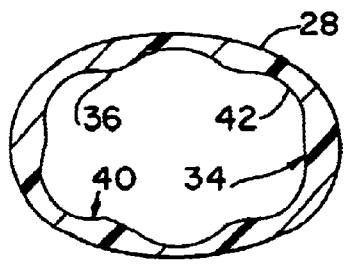
Figure 2H:
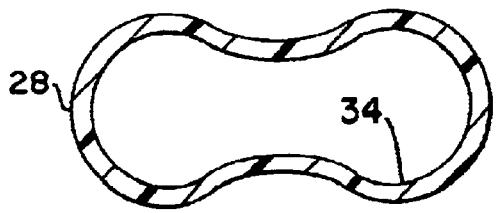

In FIG. 2f, this embodiment's interior sidewall 34 contains a number of flutes 40 which have arcuate segments or valleys 42 and peaks 36. This yields an undulating contour. FIG. 2g illustrates an embodiment which is generally oval in shape, but also contains undulations or flutes 40. FIG. 2h shows yet another embodiment having a "peanut-like" shape, with a constricted central part yielding an undulating contour.

Figure 3:
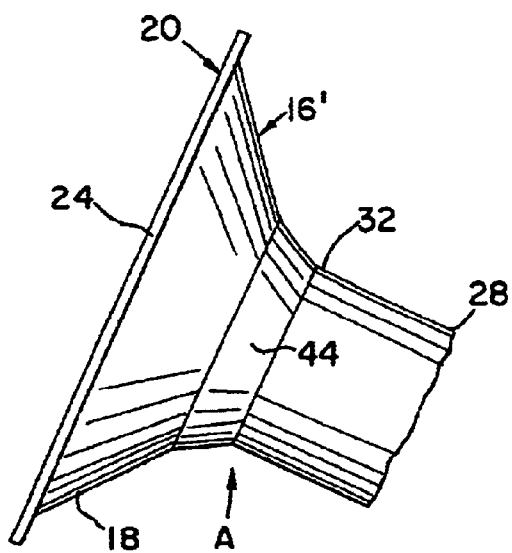
FIG. 3 shows a side view of a breastshield conical portion and tubular extension having a chamfered transition into the tubular extension made in accordance with another aspect of the invention.

To increase the comfort of the breastshield 10, an improved breast-receiving conical portion 16' is shown in FIG. 3. This breastshield 16' is provided with a smoother or less abrupt transition from the main cone area to the tubular extension 28.

Turning to FIG. 3, conical portion 16' has an intermediate zone which is of a different slope from that of the main part of the cone. This forms a chamfer 44, which has a greater slope than that of the main cone, but less than that of the tubular extension 28. The angle between the conical portion 16' and the tubular extension 28 at the opening 32 is therefore less sharp.

Figure 4:
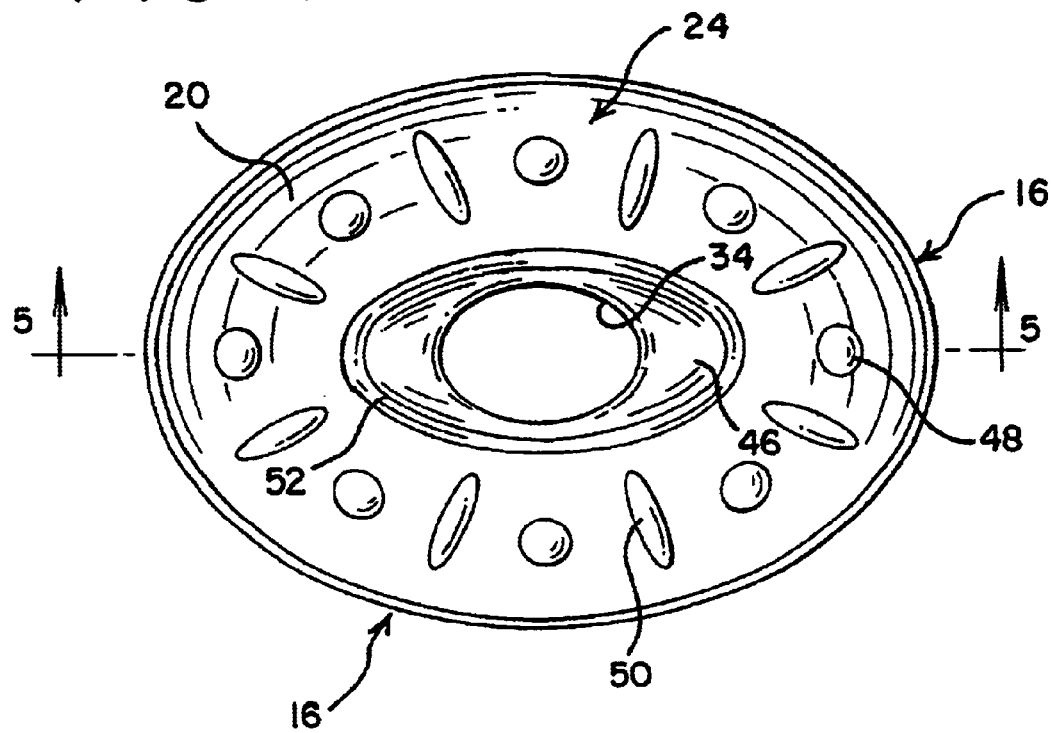
FIG. 4 is a view looking into a breastshield, and shows another variation having a non-circular tubular extension as well as non-circular main breast-receiving part, with various-shaped protuberances on the main part itself.
Figure 5:
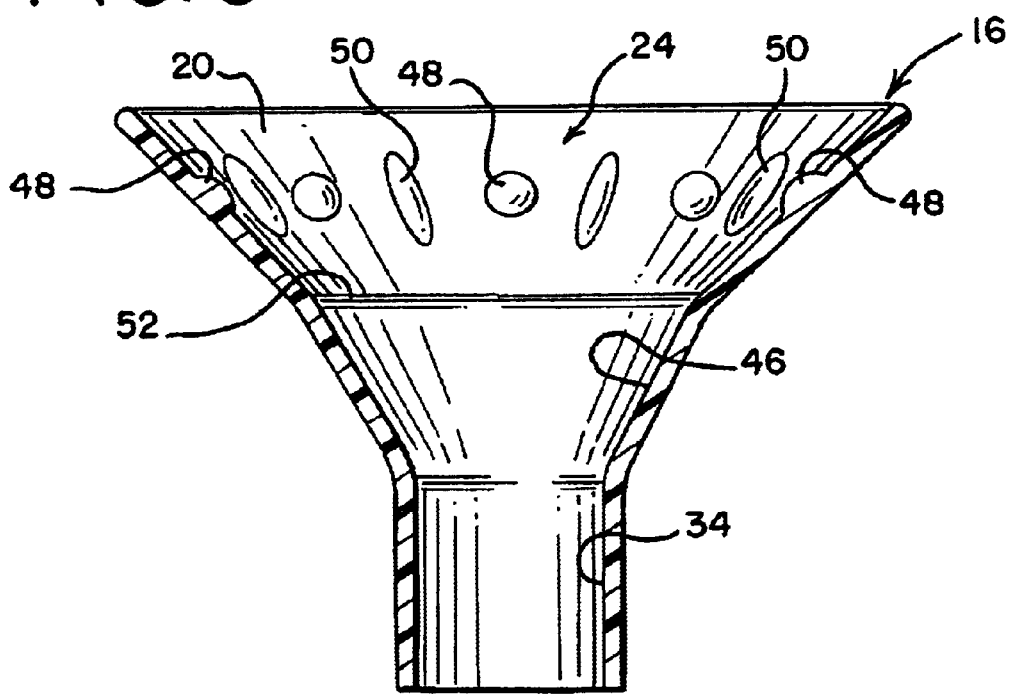
FIG. 5 is a sectional view taken along line 5—5 of FIG. 4.

FIGS. 4 and 5 show a conceptualized breastshield having a number of different features shown thereon. As will be understood, one or more of these features could be utilized to advantage, and all need not be employed together.

The FIG. 4 embodiment has a nipple tunnel with an oval shape such as shown in FIG. 2a. This shape extends into the main (base) 24 breast-receiving part of the breastshield, however, with a transition area 46 extending from the long axis of the oval. This transition area 46 essentially is an indented part of the base 24 which provides a smoother transition into the nipple tunnel interior sidewall 34, while also serving to conform the breast to the transition shape in this area. The other nipple tunnel interior configurations described above could likewise be extended into the breastshield base 24 in a similar fashion.

Additionally, the FIG. 4 embodiment includes hemispherical bumps 48, elongated humps 50, and ridges or ribs 52 (only one of which is shown, for clarity), the latter roughly surrounding the transition area 46. These protuberances variously serve to provide tactile sensations for the breast (and to the extent incorporated in the tubular extension 28, the nipple as well), different from the standard smooth shape of the breastshield interior surface. This embodiment has the shapes upstanding relative to the base, and rigid or semi-rigid in form.

It should also be borne in mind that the generally rigid conical shape described with respect to the main part or base 24 need not be so formed. Many attributes of the present invention will find application with a soft breast conforming portion, for instance, as well as a breast-receiving portion which is tubular (e.g., more adapted for engaging the nipple and closely adjacent breast than substantial breast surface area), among other non-conical shapes.

Thus, while the invention has been described with respect to certain presently preferred embodiments, those with skill in the art will recognize changes, modifications and other applications which will fall within the scope of the inventive concepts and claims.

What is claimed is:

1. An improved breastshield having a generally rigid breast-receiving portion with a generally rigid extension within which a nipple is receivable, comprising:
   an interior contour for said breast-receiving portion upon which are formed a combination of at least two types in plurality of different-shaped surface features selected from a group consisting of hemispherical bumps, elongate humps, ridges and ribs, over which a breast moves in use of the breastshield and wherein said surface features are also formed in said extension over which a nipple moves in use of the breastshield.

2. An improved breastshield for a breastpump comprising:
   a main breast-receiving portion having a downstream opening, an exterior and an interior;
   a generally rigid tubular extension, which does not collapse and retains its shape during use, having a proximal end that extends from and communicates with the opening of the breast-receiving portion;
   said tubular extension having an interior sidewall surface with a non-circular circumferential contour along at least a part of an axial length of said tubular extension adjacent said proximal end, wherein said non-circular circumferential contour is triangular in shape.

3. An improved breastshield for a breastpump comprising:
   a main breast-receiving portion having a downstream opening, an exterior and an interior;
   a generally rigid tubular extension, which does not collapse and retains its shape during use, having a proximal end that extends from and communicates with the opening of the breast-receiving portion;
   said tubular extension having an interior sidewall surface with a non-circular circumferential contour along at least a part of an axial length of said tubular extension adjacent said proximal end, wherein said non-circular circumferential contour is rectangular in shape.

4. An improved breastshield for a breastpump comprising:
   a main breast-receiving portion having a downstream opening, an exterior and an interior;
   a generally rigid tubular extension, which does not collapse and retains its shape during use, having a proximal end that extends from and communicates with the opening of the breast-receiving portion;

said tubular extension having an interior sidewall surface with a non-circular circumferential contour along at least a part of an axial length of said tubular extension adjacent said proximal end, wherein said non-circular circumferential contour is pentagonal in shape.

5. An improved breastshield for a breastpump comprising:

main breast-receiving portion having a downstream opening, an exterior and an interior;

a generally rigid tubular extension, which does not collapse and retains its shape during use, having a proximal end that extends from and communicates with the opening of the breast-receiving portion;

said tubular extension having an interior sidewall surface with a non-circular circumferential contour along at least a part of an axial length of said tubular extension adjacent said proximal end, wherein said non-circular circumferential contour is hexagonal in shape.

* * * * *